United States Patent [19]
Eberhardt et al.

[11] 3,948,943
[45] Apr. 6, 1976

[54] AMINOCARBOXYLIC ACID HIGHER ALKYLAMIDES

[75] Inventors: Hans Eberhardt; Rolf Stefan Brickl, Biberach and der Riss, Germany

[73] Assignee: Boehringer Ingelheim GmbH, Ingelheim am Rhein, Germany

[22] Filed: Apr. 29, 1974

[21] Appl. No.: 464,834

[30] Foreign Application Priority Data
May 3, 1973 Germany............................ 2322232

[52] U.S. Cl. .... 260/326.45; 260/558 A; 260/561 A; 424/65; 424/274; 424/324
[51] Int. Cl.² ............... C07D 207/26; C07C 103/75; C07C 103/50
[58] Field of Search........ 260/326.45, 651 A, 558 A

[56] References Cited
OTHER PUBLICATIONS
Angier et al., *Chem. Abs.*, Vol. 51: 17880h, (1957), abs. of *J. Org. Chem.* 21: 1540–1543.
Sauer et al., *Chem. Abs.*, Vol. 32: 2532⁸ (1938), abs. of *J. Am. Chem. Soc.* 60: 402–406.
Wiley et al., *Chem. Abs.*, Vol. 44: 7768c (1950), abs. of *J. Am. Chem. Soc.*, 71: 2899–2900.

*Primary Examiner*—R. Gallagher
*Assistant Examiner*—Mark L. Berch
*Attorney, Agent, or Firm*—Hammond & Littell

[57] ABSTRACT
Compounds of the formula

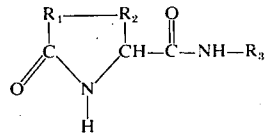

wherein
$R_1$ is lower alkyl or aryl,
$R_2$ is hydrogen or, together with $R_1$, ethylene, and
$R_3$ is straight or branched alkyl of 8 to 22 carbon atoms;
the compounds have useful therapeutic, dermatological and cosmetic properties.

4 Claims, No Drawings

AMINOCARBOXYLIC ACID HIGHER ALKYLAMIDES

This invention relates to novel higher alkylamides of aminocarboxylic acids, as well as to a process for preparing these compounds.

More particularly, the present invention relates to a novel class of aminocarboxylic acid higher alkylamides represented by the formula

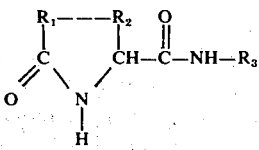

wherein
$R_1$ is lower alkyl or aryl, especially methyl or phenyl,
$R_2$ is hydrogen or, together with $R_1$, ethylene, and
$R_3$ is straight or branched alkyl of 8 to 22 carbon atoms, especially 2-ethyl-n-hexyl, n-octyl, n-decyl, n-dodecyl, n-tetradecyl, n-hexadecyl, n-octadecyl or n-docosyl.

The compounds embraced by formula I may be prepared by reacting a compound of the formula

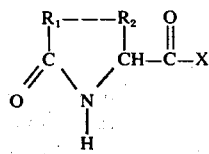

wherein
$R_1$ and $R_2$ have the same meanings as in formula I, and
X is hydroxyl, chlorine, bromine, iodine, alkoxy, aryloxy or acyloxy,
with a primary amine of the formula

wherein $R_3$ has the same meanings as in formula I. The reaction is optionally performed in a solvent, such as pyridine, benzene, toluene or chloroform, and optionally in the presence of an acid-binding agent, such as sodium carbonate or triethylamine. Depending upon the reactivity of substituent X in formula II, the reaction is carried out at temperatures between −20° and +200°C.

When X is hydroxyl, it is of advantage if the reaction is performed in the presence of an acid-activating agent, such as thionyl chloride or N,N'-dicyclohexylcarbodiimide; however, it is particularly advantageous to simultaneously use an amine of the formula III as the solvent medium. The reacton will, however, also proceed without a solvent.

The starting compounds of the formulas II and III are described in the literature.

The following examples further illustrate the present invention and will enable others skilled in the art to understand it more completely. It should be understood, however, that the invention is not limited solely to the particular examples given below.

EXAMPLE 1

N-Benzoyl-glycine n-dodecylamide

A mixture consisting of 10 gm (0.056 mol) of N-benzoyl-glycine and 10.5 gm (0.056 mol) of n-dodecylamine was heated for 90 minutes at 160°C., while stirring. Thereafter, ethyl acetate and activated charcoal were added to the reaction mixture, and the mixture was vacuum-filtered while still hot. Upon cooling of the filtrate, a crystalline substance separated out which was collected and again recrystallized from ethyl acetate, yielding 11.9 gm (58% of theory) of the compound of the formula

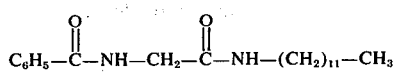

having a melting point of 124°C.

EXAMPLE 2

5-Oxo-2-pyrrolidine carboxylic acid n-dodecylamide

While cooling and stirring a mixture consisting of 9.2 gm (0.05 mol) of n-dodecylamine and 50 ml of pyridine, 17.3 gm (0.05 mol) of 5-oxo-2-pyrrolidine carboxylic acid chloride were added thereto in small portions, and the resulting mixture was stirred for one hour at room temperature. Thereafter, the reaction mixture was admixed with water, acidified and extracted with chloroform. The organic phase was separated, washed with water, dried and evaporated. The residue was recrystallized from ethyl acetate, yielding 9.0 gm (62% of theory) of the compound of the formula

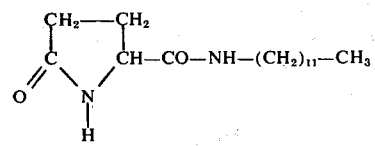

which had a melting point of 114°-116°C.

EXAMPLE 3

N-Acetyl-glycine n-docosylamide a. Ethyl N-acetyl-glycinate 31 gm of acetic acid anhydride were slowly added to a solution of ethyl glycinate (prepared from 31 gm ethyl glycinate hydrochloride in ether and sodium hydroxide) in 70 ml of pyridine, while stirring and cooling the solution. The resulting mixture was then stirred for one hour at room temperature and subsequently evaporated, yielding 15 gm (55% of theory) of ethyl N-acetyl-glycinate.

b. A mixture consisting of 1.13 gm (0.01 mol) of ethyl N-acetyl-glycinate and 2.50 gm (0.0078 mol) of n-docosyl-amine was heated for 90 minutes at 150°C., while stirring. Thereafter, ethyl acetate was added to the hot reaction mixture, and upon cooling of the mixture a crystalline substance separated out which was collected and again recrystallized from ethyl acetate in the presence of activated charcoal and silicagel. 1.5 gm (55% of theory) of the compound of the formula

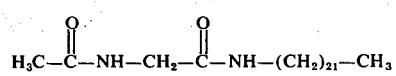

having a melting point of 135°–137°C. were obtained.

EXAMPLE 4

Using a procedure analogous to that described in Example 2, 5-oxo-2-pyrrolidine carboxylic acid n-octyl-amide, m.p. 112°–113°C., was prepared from 5-oxo-2-pyrrolidine carboxylic acid chloride and n-octyl-amine.

EXAMPLE 5

Using a procedure analogous to that described in Example 2, 5-oxo-2-pyrrolidine carboxylic acid n-decyl-amide, m.p. 112°C., was prepared from 5-oxo-2-pyrrolidine carboxylic acid chloride and n-decyl-amine.

EXAMPLE 6

Using a procedure analogous to that described in Example 2, 5-oxo-2-pyrrolidine carboxylic acid n-tetradecylamide, m.p. 113°C., was prepared from 5-oxo-2-pyrrolidine carboxylic acid chloride and n-tetradecyl-amine.

EXAMPLE 7

Using a procedure analogous to that described in Example 2, 5-oxo-2-pyrrolidine carboxylic acid n-hexadecylamide, m.p. 114°–116°C., was prepared from 5-oxo-2-pyrrolidine carboxylic acid chloride and n-hexadecyl-amine.

EXAMPLE 8

Using a procedure analogous to that described in Example 2, 5-oxo-2-pyrrolidine carboxylic acid n-octadecylamide, m.p. 110°–112°C., was prepared from 5-oxo-2-pyrrolidine carboxylic acid chloride and n-octadecyl-amine.

EXAMPLE 9

Using a procedure analogous to that described in Example 2, 5-oxo-2-pyrrolidine carboxylic acid n-docosylamide, m.p. 114°–116°C., was prepared from 5-oxo-2-pyrrolidine carboxylic acid chloride and n-docosyl-amine.

EXAMPLE 10

Using a procedure analogous to that described in Example 2, 5-oxo-2-pyrrolidine carboxylic acid (2-ethylhexyl)-amide, m.p. 100°–102°C., was prepared from 5-oxo-2-pyrrolidine carboxylic acid chloride and (2-ethyl-hexyl)-amine.

EXAMPLE 11

Using a procedure analogous to that described in Example 3, N-acetyl-glycine n-octyl-amide, m.p. 139°–140°C., was prepared from ethyl N-acetyl-glycinate and n-octylamine.

EXAMPLE 12

Using a procedure analogous to that described in Example 3, N-acetyl-glycine n-decyl-amide, m.p. 145°–147°C., was prepared from ethyl N-acetyl-glycinate and n-decylamine.

EXAMPLE 13

Using a procedure analogous to that described in Example 3, N-acetyl-glycine n-dodecyl-amide, m.p. 143°C., was prepared from ethyl N-acetyl-glycinate and n-dodecylamine.

EXAMPLE 14

Using a procedure analogous to that described in Example 3, N-acetyl-glycine n-tetradecyl-amide, m.p. 145°C., was prepared from ethyl N-acetyl-glycinate and n-tetradecylamine.

EXAMPLE 15

Using a procedure analogous to that described in Example 3, N-acetyl-glycine n-hexadecyl-amide, m.p. 145°–146°C., was prepared from ethyl N-acetyl-glycinate and n-hexadecyl-amine.

EXAMPLE 16

Using a procedure analogous to that described in Example 3, N-acetyl-glycine n-octadecyl-amide, m.p. 145°C., was prepared from ethyl N-acetyl-glycinate and n-octadecylamine.

EXAMPLE 17

Using a procedure analogous to that described in Example 1, N-benzoyl-glycine n-octyl-amide, m.p. 118°C., was prepared from N-benzoyl-glycine and n-octyl-amine.

EXAMPLE 18

Using a procedure analogous to that described in Example 1, N-benzoyl-glycine n-decyl-amide, m.p. 122°C., was prepared from N-benzoyl-glycine and n-decyl-amine.

EXAMPLE 19

Using a procedure analogous to that described in Example 1, N-benzoyl-glycine n-tetradecyl-amide, m.p. 124°C., was prepared from N-benzoyl-glycine and n-tetradecyl-amine.

EXAMPLE 20

Using a procedure analogous to that described in Example 1, N-benzoyl-glycine n-hexadecyl-amide, m.p. 125°C., was prepared from N-benzoyl-glycine and n-hexadecyl-amine.

EXAMPLE 21

Using a procedure analogous to that described in Example 1, N-benzoyl-glycine n-octadecyl-amide, m.p. 123°C., was prepared from N-benzoyl-glycine and n-octadecyl-amine.

EXAMPLE 22

Using a procedure analogous to that described in Example 1, N-benzoyl-glycine n-docosyl-amide, m.p. 128°–130°C., was prepared from N-benzoyl-glycine and n-docosylamine.

The compounds of the present invention, that is, those embraced by formula I above, have useful therapeutic and cosmetic properties. More particularly, the compounds of this invention exhibit sebaceous gland excretion-inhibiting, antiphlogistic, antiproliferative, dandruff-suppressing, capillary-stabilizing and skin-moisturizing activities in warm-blooded animals.

The sebaceous gland excretion-inhibiting activity was ascertained by the glass block method described by Schaefer and Kuhn-Bussius in Arch. Klin. exper. Derm. 238, 429–435 (1970). Small glass blocks, the facets of which have been roughened or frosted, are pressed against the skin surface where the amount of skin fat is measured. The skin fat or sebum transferred from the skin to the glass facet makes the blocks more translucent, and the increase in translucence is directly proportional to the amount of sebum present on the skin area. The translucence is measured in a photometer. Prior to measurement of the degree of re-fatting of the skin, the skin fat was removed with a plastic coil.

0.25 ml of an ethanolic 5% solution of the compound to be tested was applied to half of the forehead of five to 10 human test subjects, while 0.25 ml of ethanol was applied to half of the forehead of a group of 5 to 10 control subjects. After 90 minutes the skin fat was removed with the plastic foil, and after three additional hours the degree of re-fatting was determined with the aid of the small glass blocks referred to above. The following results were obtained:

| Compound | Number of Test Subjects | Average Controls | extinction values Treated | Difference |
|---|---|---|---|---|
| 5-Pyrrolidone-(2)-carboxylic acid n-dodecylamide | 5 | 61.0 | 74.0 | 13.0 |
| 5-Pyrrolidone-(2)-carboxylic acid n-hexadecylamide | 5 | 70.0 | 77.5 | 7.5 |

The antiphlogistic activity of the compounds of the present invention was ascertained by the dinitrochlorobenzene-eczema method [see A. I. Scott, Brit. J. Dermatol. 77, 586 (1965)].

The compound to be tested was applied in the form of an ethanolic 5% solution to the shaved flanks of a group of 10 guinea pigs which had been sensitized with dinitrochlorobenzene. An analogous control group was treated with only ethanol. The treatment was effected 30 minutes prior to release of the allergic reaction with a 1% solution of dinitrochlorobenzene in acetone. The results were visually evaluated 5 and 7 hours thereafter. The following results, averaged from the two readings, were obtained:

| Compound | Inhibition of dinitrochlorobenzene-eczema over controls in % |
|---|---|
| 5-Pyrrolidone-(2)-carboxylic acid n-dodecylamide | 59 |
| 5-Pyrrolidone-(2)-carboxylic acid n-tetradecylamide | 51 |
| 5-Pyrrolidone-(2)-carboxylic acid n-hexadecylamide | 56 |
| 5-Pyrrolidone-(2)-carboxylic acid n-octadecylamide | 48 |
| N-Acetyl-glycine n-dodecyl-amide | 34 |
| N-Acetyl-glycine-n-octadecyl-amide | 54 |
| N-Benzoyl-glycine n-octyl-amide | 41 |
| N-Benzoyl-glycine n-hexadecyl-amide | 43 |

The compounds of the formula I were found to be practically non-toxic, as determined in mice by conventional methods. For example, 5-pyrrolidone-(2)-carboxylic acid hexadecylamide was found to have an $LD_{50}$ of greater than 4000 mgm/kg i.p.

For cosmetic and/or therapeutic treatment of the skin the compounds embraced by formula I are incorporated in conventional manner into conventional forms of topical dermatological compositions at a concentration of 0.1 to 10%, preferably 0.5 to 5%, by weight based on the total weight of the composition. Such conventional forms of topical compositions include ointments, creams, aerosols, powders, tinctures, gels, pastes and lotions intended for use in the care and treatment of the skin, and such compositions may, in addition, contain one or more other active ingredients, such as vitamins, corticosteroids, steroids, anti-histamines, keratolytics, antibiotics or disinfectants.

The following examples illustrate a few topical compositions for the cosmetic and/or therapeutic treatment of the skin, which comprise a compound of the formula I. The parts are parts by weight unless otherwise specified.

EXAMPLE 23

Cream

The cream composition is compounded from the following ingredients:

| | | |
|---|---|---|
| 5-Pyrrolidone-(2)-carboxylic acid hexadecylamide | 3.0 | parts |
| Benzalkonium chloride | 0.1 | '' |
| Cremophor O[1] | 4.0 | '' |
| Glycerin monostearate | 4.0 | '' |
| Lanette O[2] | 5.0 | '' |
| Spermaceti | 3.0 | '' |
| Cetiol V[3] | 10.0 | '' |
| Distilled water | q.s.ad 100.0 | '' |

[1]Long-chain, high-molecular, water-soluble, wax-like polyglycolether; a commercial cosmetic and pharmaceutical emulsifier for high-molecular alcohols, fatty acids, waxes, wool grease, spermaceti, etc.
[2]Mixture of cetyl and stearyl alcohols; a commercial neutral, skin-compatible, consistancy-imparting factor for ointments, creams and emulsions.
[3]Mixture of esters of unsaturated fatty acids, mainly oleyl oleate; a commercial, conventional, skin-penetrating, low-viscosity liquid additive for cosmetic creams and the like.

Preparation:

The benzalkonium chloride is dissolved in the distilled water at 70°C. (I). The pyrrolidone-carboxamide is homogeneously suspended in the molten (70°C.) mixture of the Cremophor, the glycerin monostearate, the Lanette, the spermaceti and the Cetiol (II). Suspension II is emulsified at 70°C. into solution I, and the composition is stirred until cool.

EXAMPLE 24

Ointment

The ointment is compounded from the following ingredients:

| | | |
|---|---|---|
| 5-Pyrrolidone-(2)-carboxylic acid hexadecylamide | 3.0 | parts |
| Cremophor 0 | 6.0 | " |
| Wool grease | 2.0 | " |
| Paraffin oil | 45.0 | " |
| Vaseline q.s.ad | 100.0 | " |
| Cremophor A solid[4] | 1.0 | " |

[4]Non-ionic derivative of fatty substance with polyethylene-oxide radical; a commercial water-dispersible emulsifier for paraffin oil, vaseline and vegetable oils.

The Cremophors, the wool grease, the paraffin oil and the vaseline are admixed with each other, the mixture is melted by heating to 70°C., the pyrrolidone-carboxamide is suspended in the molten mixture, and the composition is stirred until cool.

EXAMPLE 25

Gel

The gel is compounded from the following ingredients:

| | | |
|---|---|---|
| 5-Pyrrolidone-(2)-carboxylic acid hexadecylamide | 3.0 | parts |
| Carbopol 940[5] | 0.6 | " |
| Triethanolamine | 0.6 | " |
| Cremophor EL[6] | 5.0 | " |
| Isopropanol | 30.0 | " |
| Distilled water q.s.ad | 100.0 | " |

[5]Carboxypolymethylene; carboxyvinyl polymer with very high molecular weight; forms colloidal solutions with water; a commercial thickening agent for cosmetics.
[6]A viscous oil similar in composition to Cremophor O and A; a commercial emulsifier for cosmetics.

Preparation:

The pyrrolidone-carboxamide, the Cremophor and the triethanolamine are dissolved in the isopropanol, and the resulting solution is stirred into the solution of the Carbopol in the distilled water.

EXAMPLE 26

Bath Oil

The composition is compounded from the following ingredients:

| | | |
|---|---|---|
| 5-Pyrrolidone-(2)-carboxylic acid hexadecylamide | 5.0 | parts |
| Texapon N 25[7] | 30.0 | " |
| Comperlan OD[8] | 5.0 | " |
| Isopropanol | 20.0 | " |
| Ethereal Oil | 2.0 | " |
| Distilled water q.s.ad | 100.0 | " |

[7]Fatty alcohol ether sulfate; a commercial washing, wetting and dispersing agent.
[8]A fatty acid alkylolamide; commercial consistency-imparting factor for cosmetic and pharmaceutical preparations.

Preparation:

The pyrrolidone-carboxamide and the ethereal oil are dissolved in the isopropanol, and the resulting solution is stirred into the solution of the Texapon and the Comperlan in the distilled water.

EXAMPLE 27

Hair Tonic

The composition is compounded from the following ingredients:

| | | |
|---|---|---|
| 5-Pyrrolidone-(2)-carboxylic acid hexadecylamide | 0.5 | parts |
| Diisopropyl adipate | 0.2 | " |
| Perfume oil | 0.1 | " |
| Isopropanol | 50.0 | " |
| Distilled water q.s.ad | 100.0 | " |

Preparation:

The pyrrolidone-carboxamide, the adipate and the perfume oil are dissolved in the isopropanol, and the resulting solution is admixed with the distilled water by stirring.

EXAMPLE 28

Aerosol Dry Spray

The spray is compounded from the following ingredients:

| | | |
|---|---|---|
| 5-Pyrrolidone-(2)-carboxylic acid hexadecylamide | 3.0 | parts |
| Span 85 | 0.4 | " |
| Frigen 11 A | 3.0 | " |
| Frigen 12/114 (40:60) | 93.6 | " |

Preparation:

The pyrrolidone-carboxamide, the Span and the Frigen 11 are intimately admixed in a ball mill, the mixture is cooled to −15°C. and slowly introduced into the Frigen 12/114 mixture at −40° to −50°C., and the composition is filled into aerosol containers, accompanied by stirring.

EXAMPLE 29

Aerosol Foam

The foam composition is compounded from the following ingredients:

| | | |
|---|---|---|
| 5-Pyrrolidone-(2)-carboxylic acid hexadecylamide | 3.0 | parts |
| Cremophor EL | 1.0 | " |
| Tween 80 | 1.2 | " |
| Texapon N 25 | 0.8 | " |
| Ethanol (94%) | 21.0 | " |
| Distilled water | 57.0 | " |
| Frigen 12/114 (60:40) | 16.0 | " |

Preparation:

The pyrrolidone-carboxyamide is dissolved in the ethanol (solution I). The Cremophor, the Tween and the Texapon are dissolved in the distilled water (solution II). Solution I is stirred into Solution II, and the resulting concentrate is filled into aerosol cans. After the valve has been affixed to the filled cans, the propellant gas mixture is introduced under pressure.

EXAMPLE 30

Cream

The composition is compounded from the following ingredients:

| | | |
|---|---|---|
| 5-Pyrrolidone-(2)-carboxylic acid dodecylamide | 3.0 | parts |
| Benzalkon A | 0.1 | " |
| Cremophor O | 4.0 | " |
| Glycerin monostearate | 4.0 | " |
| Lanette O | 5.0 | " |
| Spermaceti | 3.0 | " |
| Cetiol V | 10.0 | " |
| Vitamin A acetate | 30,000 I.U. | |
| Vitamin E acetate | 20 I.U. | |
| Distilled water q.s.ad | 100.0 | " |

The composition is compounded in a manner analogous to that described in Example 23.

EXAMPLE 31

Lotion

The lotion is compounded from the following ingredients:

| | | |
|---|---|---|
| 5-Pyrrolidone-(2)-carboxylic acid hexadecylamide | 3.0 | parts |
| Span 40 | 1.0 | " |
| Cremophor O | 2.0 | " |
| Lanette O | 2.0 | " |
| Spermaceti | 1.0 | " |
| Cetiol V | 5.0 | " |
| Paraffin oil, soluble | 1.0 | " |
| Methylparaben | 0.1 | " |
| Distilled water q.s.ad | 100.0 | " |

Preparation:

The Span, the Cremophor, the Lanette, the spermaceti, the Cetiol and the paraffin oil are admixed with each other, the mixture is melted at 70°C., and the pyrrolidonecarboxamide is dissolved in the molten mixture. The distilled water is heated to 80°C., the methylparaben is dissolved therein, the resulting solution is cooled to 70°C. and added to the molten fatty mixture, and the composition is homogenized and stirred until cool.

EXAMPLE 32

Shampoo

The shampoo is compounded from the following ingredients:

| | | |
|---|---|---|
| 5-Pyrrolidone-(2)-carboxylic acid hexadecylamide | 3.0 | parts |
| Texapon N 25 | 48.0 | " |
| Comperlan O D | 7.0 | " |
| Methyl cellulose | 1.0 | " |
| Perfume oil | 0.2 | " |
| Methylparaben | 0.5 | " |
| Distilled water q.s.ad | 100.0 | |

Preparation:

The distilled water is heated to 80°C., the methylparaben is dissolved therein, and the methyl cellulose is suspended in the aqueous solution. The Texapon, the Comperlan and the perfume oil are admixed with each other, the pyrrolidone-carboxamide is dispersed in the mixture with a high-speed stirrer, the dispersion is added to the methyl cellulose slurry, and the resulting composition is homogenized and purged of air.

EXAMPLE 33

Powder

The powder is compounded from the following ingredients:

| | | |
|---|---|---|
| 5-Pyrrolidone-(2)-carboxylic acid hexadecylamide | 3.0 | parts |
| Colloidal silicic acid | 1.0 | " |
| Magnesium stearate | 0.2 | " |
| ANM corn starch q.s.ad | 100.0 | " |

Preparation:

The pyrrolidone-carboxamide, the colloidal silicic acid and the magnesium stearate are successively added to about one-third of the indicated amount of the corn starch, the mixture is thoroughly blended, the remaining amount of corn starch is added thereto, and the resulting composition is again thoroughly blended.

EXAMPLE 34

Paste

The paste is compounded from the following ingredients:

| | | |
|---|---|---|
| 5-Pyrrolidone-(2)-carboxylic acid octadecylamide | 3.0 | parts |
| Lanogen 1500[9] | 20.0 | " |
| Isopropanol | 45.0 | parts |
| Veegum[10] pharm. | 10.0 | " |
| Pigment + dye | 1.0 | " |
| Perfume oil | 0.2 | " |
| Distilled water q.s.ad | 100.0 | " |

[9]A commercial ointment base made from polyethyleneglycol.
[10]Flocculated colloidal magnesium aluminum silicate; a commercial emulsifying, suspending and thickening agent.

Preparation:

The pyrrolidone-carboxamide is dissolved in the ointment base at 60°C. (solution I). The perfume oil is dissolved in the isopropanol (solution II). The distilled water is heated to 60°C., the Veegum is dispersed therein and allowed to swell, solutions I and II and the pigment and dye are added thereto, and the composition is thoroughly kneaded and homogenized.

EXAMPLE 35

Tincture

The tincture is compounded from the following ingredients:

| | | |
|---|---|---|
| 5-Pyrrolidone-(2)-carboxylic acid hexadecylamide | 3.0 | parts |
| Isopropanol | 25.0 | " |
| Ethanol (96%), pure | 25.0 | " |
| Perfume oil | 0.2 | " |
| Distilled water q.s.ad | 100.0 | " |

Preparation:

The isopropanol is admixed with the ethanol, the mixture is heated to 60°C., the pyrrolidone-carboxamide and the perfume oil are dissolved therein, the distilled water is added to the solution, and the resulting aqueous mixture is cooled to room temperature and filtered.

Gel with Antibiotic

The gel is compounded from the following ingredients:

| | | | |
|---|---|---|---|
| 5-Pyrrolidone-(2)-carboxylic acid hexadecylamide | | 3.0 | parts |
| Chloramphenicol or tetracycline | . HCl | 0.1 | " |
| Salicylic acid | | 0.5 | " |
| Isopropanol | | 25.0 | " |
| Bentone EW[1] | | 2.0 | " |
| Triethanolamine | | 1.8 | " |
| Distilled water | q.s.ad | 100.0 | " |

[1]Organic derivatives of hydrous magnesium aluminum silicate minerals; a commercial gelling agent for viscosity and flow control.

Preparation:

The Bentone is stirred with a high-speed stirrer into about two-thirds of the required amount of distilled water and allowed to swell therein (I). The salicylic acid and the triethanolamine are dissolved in the remainder of the water (II). The pyrrolidone-carboxamide and the antibiotic are dissolved in the isopropanol (III). II and III are added to I while stirring, and the resulting composition is homogenized and purged of air.

While the above composition examples illustrate only three of the compounds of the formula I as active ingredients, it should be understood that any of the other compounds embraced by formula I may be substituted therefor in Examples 23 through 36.

Likewise, the amount of active ingredient in these illustrative examples may be varied to achieve the concentration range set forth above, and the amounts and nature of the inert carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula

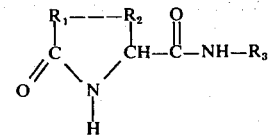

wherein
$R_1$ is methyl or phenyl,
$R_2$ is hydrogen or, together with $R_1$, ethylene, and
$R_3$ is straight or branched alkyl of 8 to 22 carbon atoms.

2. The compound of claim 1 which is 5-pyrrolidone-(2)-carboxylic acid n-hexadecylamide.

3. The compound of claim 1 which is 5-pyrrolidone-(2)-carboxylic acid n-dodecylamide.

4. The compound of claim 1 which is 5-pyrrolidone-(2)-carboxylic acid n-octadecylamide.

* * * * *